United States Patent
Gross

(10) Patent No.: US 7,850,918 B2
(45) Date of Patent: Dec. 14, 2010

(54) MULTIPLE SAMPLE GAS SORPTION TESTER

(75) Inventor: Karl J. Gross, Fremont, CA (US)

(73) Assignee: Hy-Energy, LLC, Newark, CA (US)

( * ) Notice: Subject to any disclaimer, the term of this patent is extended or adjusted under 35 U.S.C. 154(b) by 431 days.

(21) Appl. No.: 12/060,757

(22) Filed: Apr. 1, 2008

(65) Prior Publication Data

US 2008/0253932 A1    Oct. 16, 2008

Related U.S. Application Data

(60) Provisional application No. 60/911,079, filed on Apr. 10, 2007.

(51) Int. Cl.
  *G01N 30/96*  (2006.01)
  *G01N 7/00*   (2006.01)
  *G01F 25/00*  (2006.01)
  *C12M 1/34*   (2006.01)

(52) U.S. Cl. ............... 422/88; 422/83; 436/167; 73/1.02; 73/1.73; 73/38; 435/287.5

(58) Field of Classification Search ........... 422/83, 422/88
  See application file for complete search history.

(56) References Cited

U.S. PATENT DOCUMENTS

| | | | | |
|---|---|---|---|---|
| 4,762,010 A | * | 8/1988 | Borghard et al. | 73/865.5 |
| 5,637,810 A | * | 6/1997 | Conner, Jr. | 73/865.5 |
| 6,257,835 B1 | * | 7/2001 | Kaehler | 417/205 |
| 6,981,426 B2 | * | 1/2006 | Wang et al. | 73/865.5 |
| 2006/0005608 A1 | * | 1/2006 | Kitzhoffer et al. | 73/38 |

* cited by examiner

*Primary Examiner*—Jill Warden
*Assistant Examiner*—Jennifer Wecker
(74) *Attorney, Agent, or Firm*—Patterson & Sheridan, LLP

(57) ABSTRACT

Embodiments of the invention contemplate an apparatus that determines gas sorption properties of a large number of material samples simultaneously, by sequentially measuring the pressure in a plurality of sample chambers until all chambers have reached equilibrium pressure. In most applications, it is most useful to quantify the sorption capacity of a material under specific conditions, i.e., at a certain temperature and pressure. Because sorption capacity is determined by bringing a material sample to an equilibrium state with a dosing gas, detailed kinetic data related to the sorption properties of a material are not absolutely necessary. Therefore, complete pressure-time curves are not typically necessary, and only the equilibrium pressure of a material sample for a given quantity of dosing gas is required.

21 Claims, 6 Drawing Sheets

MULTIPLE SAMPLE GAS SORPTION TESTER

CROSS-REFERENCE TO RELATED APPLICATIONS

This application claims the priority benefit of the U.S provisional patent application titled "Multiple Sample Gas Sorption Tester" having Ser. No. 60/911,079, and filed on Apr. 10, 2007.

BACKGROUND OF THE INVENTION

1. Field of the Invention

Embodiments of the present invention relate generally to devices for performing measurements on small quantities of gases or liquids, and particularly to an apparatus for performing gas sorption measurements on multiple samples of gases.

2. Description of the Related Art

Synthesis of materials using combinatorial chemistry has been used effectively to produce new materials having small variations in composition and/or structure numbering in the 10s, 100s or 1000s at a time. Such materials processing methods have led to the discovery of new and improved chemicals, pharmaceuticals, semiconductor materials and devices. However, due to the large numbers of different materials involved, combinatorial methods can only lead to timely material discovery when rapid screening of the physical characteristics of the many types of new materials produced thereby is available.

In the case of gas sorption materials, the gas sorption properties of each new material must be tested, i.e., the absorption, adsorption, desorption, physisorption, and/or chemisorption properties, and such testing for even a single sample is a lengthy and labor-intensive process. Specifically, an extensive battery of tests is conducted in which the quantity of a dosing gas that can be contained by the material is characterized at different temperatures and pressures. A sample of the material in question is held in a chamber and is either dosed with a known quantity of a dosing gas, e.g., hydrogen, or a known quantity of the dosing gas is removed from the chamber. Typically, the chamber is maintained at a constant temperature and the chamber pressure increases or decreases as dosing gas flows into or out of the material sample. The pressure in the chamber is recorded with respect to time, and a pressure-composition-temperature (PCT) curve is established for the material from the equilibrium pressures obtained with every dose of gas. Once an equilibrium state is reached for an individual dose of gas in the chamber, i.e. the absorption/desorption rate of the dosing gas approximates zero, the equilibrium pressure for the sample material at the given experimental temperature is known. Because the chamber has a known volume and temperature, the total quantity of dosing gas that has sorbed into or desorbed out of the sample material can be calculated using the ideal gas law. The absorption or desorption test is then repeated at a different pressure-higher for absorption characterization and lower for desorption characterization-until a PCT curve is generated for the sample material from the equilibrium pressures and concentrations collected from a sequence of gas doses.

The sorption tests for establishing each PCT curve are time-consuming and require very sensitive instrumentation, such as high-accuracy pressure transducers. Thus, characterizing the sorption properties of a new material is a relatively expensive and lengthy process, especially since current testing techniques do not allow rapid screening or testing across multiple samples. In light of the expanding need for characterizing large numbers of new materials, current techniques simply cannot be used to efficiently or cost effectively analyze the large numbers of different materials to be tested.

Accordingly, there is a need in the art for a technique for efficiently and accurately performing gas sorption measurements on a large number of samples.

SUMMARY OF THE INVENTION

One embodiment of the present invention sets forth an apparatus that can determine the gas sorption properties of a large number of material samples simultaneously. The apparatus includes an array of chambers containing a plurality of sealed sample chambers, each chamber having a calibrated volume for holding a material sample, a pressure transducer fluidly coupled to a manifold, a selecting valve configured to fluidly couple any one or none of the plurality of sample chambers to the manifold, and a dosing gas reservoir with an isolation valve configured to fluidly couple and decouple the dosing gas reservoir to and from the manifold. To improve accuracy, the selecting valve may be a valve with very low displacement volume, such as a rotary or sliding valve, the manifold may consist entirely of low-volume components, and each sample chamber may include a dedicated temperature measuring device.

One advantage of the disclosed apparatus is that can be used to efficiently determine gas sorption properties of a large number of material samples with a single pressure transducer.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

Embodiments of the invention contemplate an apparatus that determines gas sorption properties of a large number of material samples simultaneously, by sequentially measuring the pressure in a plurality of sample chambers until all chambers have reached equilibrium pressure. In most applications, it is particularly useful to quantify the sorption capacity of a material under specific conditions, i.e., at a certain temperature and pressure. Because sorption capacity is determined by bringing a material sample to an equilibrium state with a dosing gas, detailed kinetic data related to the sorption properties of a material are not absolutely necessary, such as transitory changes in the absorption or desorption rate of a material in a non-equilibrium state. The minimum requirement is that enough pressure-time data has been measured to determine whether near-equilibrium conditions have been achieved. The collection of a few pressure-time data points will also be sufficient to provide sorption kinetics information for individual gas doses to multiple samples. Therefore, detailed pressure-time curves are not typically necessary, and only the equilibrium pressure and concentration of a material sample for a given quantity of dosing gas is required to determine the equilibrium pressure-temperature-concentration relationship in gas-sample sorption behavior.

Figure 1:
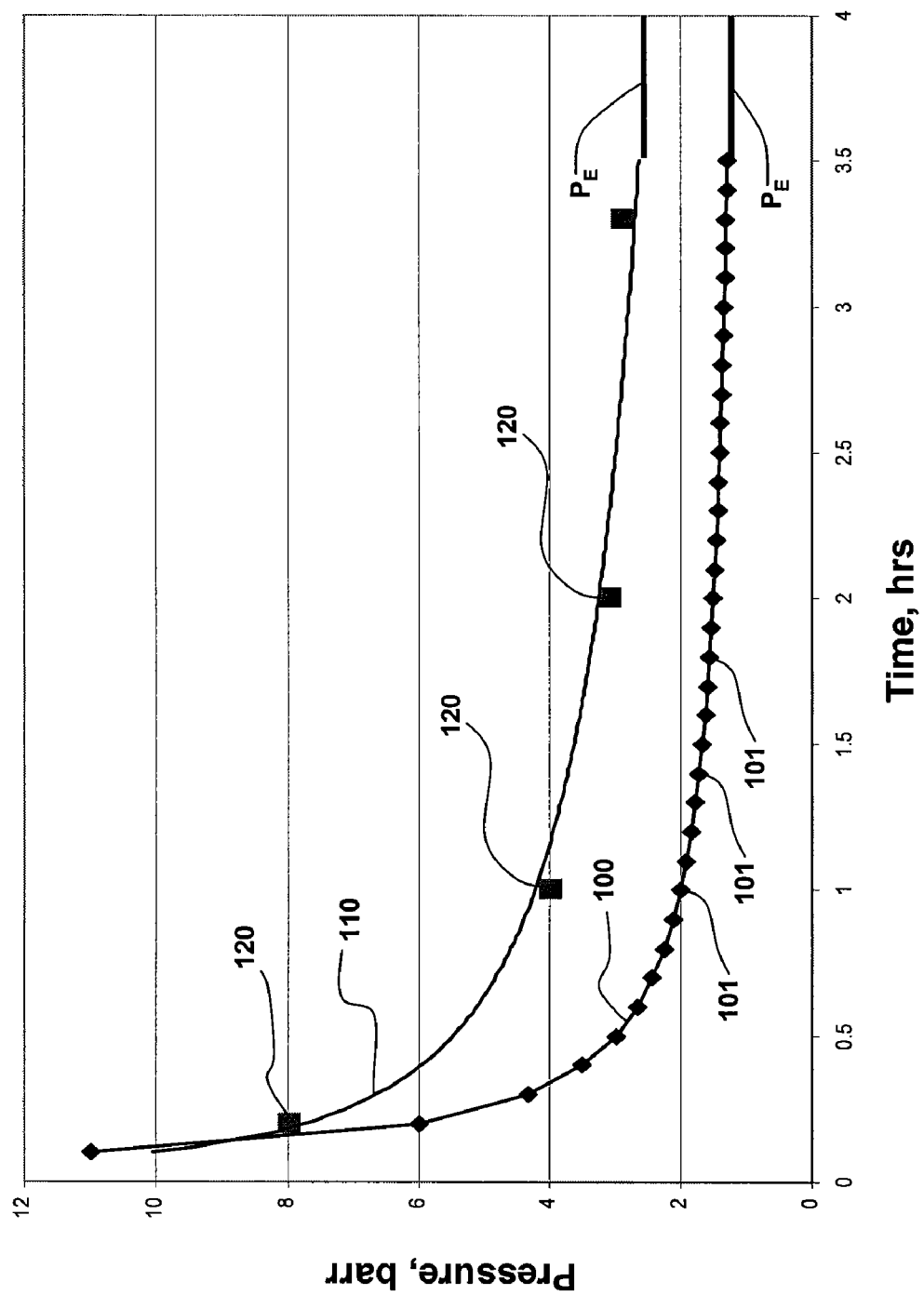
FIG. 1 illustrates two pressure-time curves.

By way of illustration, FIG. 1 illustrates two pressure-time curves 100, 110. pressure-time curve 100 has been established by taking a relatively large number of pressure measurements 101 after dosing a material sample in a sealed chamber with a dosing gas. In contrast, pressure-time curve 110 has been established by taking only four pressure measurements 120 after dosing a material sample in a sealed chamber with a dosing gas. However, the equilibrium pressure $P_E$ is readily determined for each of curves 100, 110, as illustrated in FIG. 1. This is because a relatively small number of data points are needed to accurately estimate the approach to the equilibrium pressure for a gas sorption test, in some cases as few as three. Therefore, instead of using a dedicated pressure measuring device to constantly measure the pressure in a sample chamber for the duration of a gas sorption test, it is contemplated that a single pressure measuring device can be used to sequentially measure the pressure in a plurality of sample chambers. In this way, the equilibrium pressure for a large number of material samples can be determined in a large number of gas sorption tests simultaneously.

Figure 2:
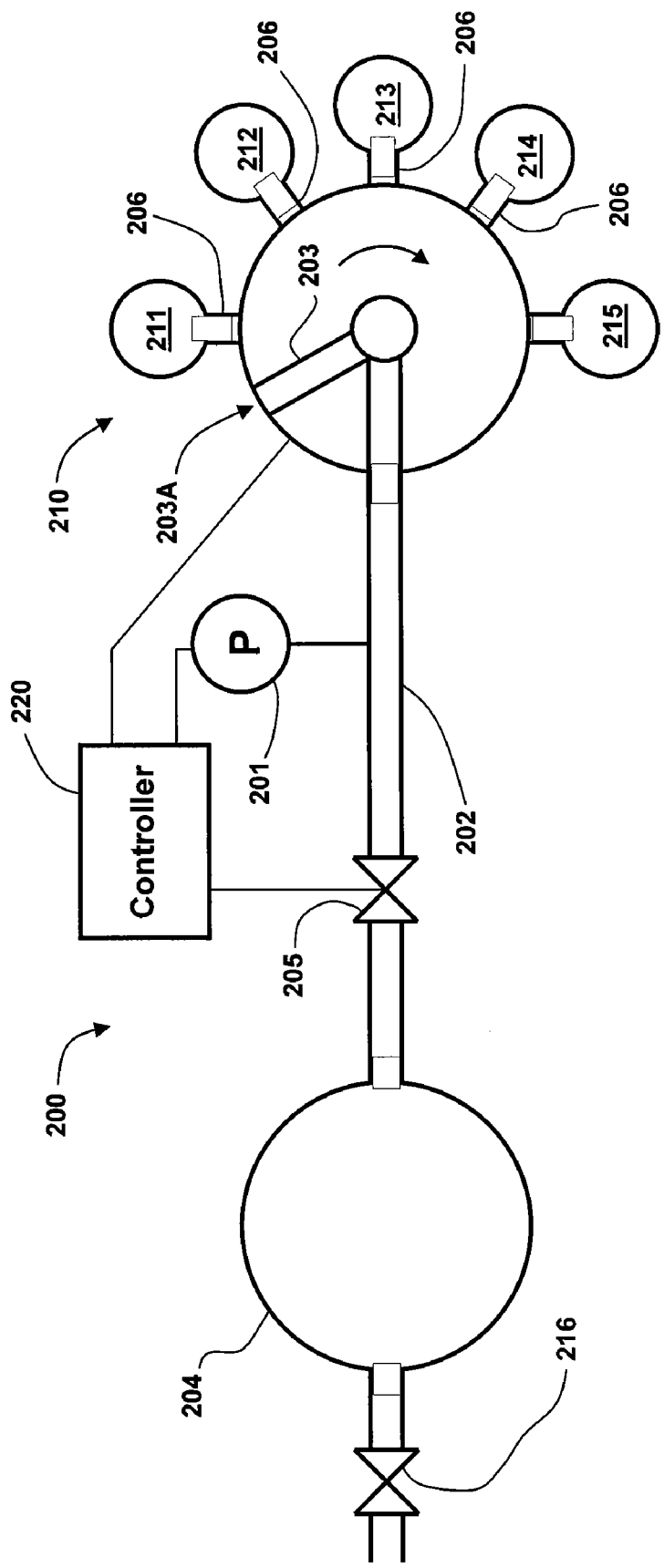
FIG. 2 illustrates a multiple sample tester, according to an embodiment of the invention.

FIG. 2 illustrates a multiple sample tester 200, according to an embodiment of the invention. Multiple sample tester 200 includes an array 210 of sample chambers 211-215, a pressure transducer 201 fluidly coupled to a manifold 202, a selecting valve 203 and a dosing gas reservoir 204. Array 210 is a rotary array and includes sample chambers 211-215. Each of sample chambers 211-215 has a known, calibrated volume, is adapted for holding a material sample during gas sorption testing, and has a large internal volume relative to the internal volume of manifold 202. "Calibrated volume," as used herein, is defined as a known volume that has been corrected to account for the volume displaced by a material sample contained in the known volume. To improve the accuracy of gas sorption measurements, each of sample chambers 211-215 may include a dedicated temperature sensor, such as a thermocouple. To further improve accuracy of gas sorption measurements, the size of the material samples tested in sample chambers 211-215 is kept as large as practicable.

Pressure transducer 201 is a high-accuracy pressure measuring device capable of detecting changes in relative or absolute pressure in manifold 202 and sample chambers 211-215 to the degree necessary for performing gas sorption tests. For example, pressure transducer may be a strain-gauge pressure transducer, a piezoelectric pressure transducer, or a capacitance manometer, such as a Model 870B Micro-Baratron®. In one embodiment, pressure transducer 201 may include an array of multiple pressure transducers, each having a different operating range. Each pressure transducer in the array may be fluidly coupled to manifold 202 individually, or via a rotating valve similar in configuration to selecting valve 203.

Manifold 202 fluidly couples pressure transducer 201 with array 210 of sample chambers 211-215 via selecting valve 203 and with dosing gas reservoir 204 via isolation valve 205. For improved accuracy, the internal volume of manifold 202 is kept very small relative to the internal volume of each of sample chambers 211-215, e.g., two orders of magnitude smaller or less. To that end, in one embodiment, manifold 202 may consist of small-diameter electropolished stainless steel tubing, having an internal diameter of 2 mm or less.

Dosing gas reservoir 204 is configured to contain a dosing gas used in gas sorption testing of material samples in multiple sample tester 200 and is recharged with the desired dosing gas after each of sample chambers 211-215 is dosed. To that end, dosing gas reservoir 204 has a calibrated volume and is designed to contain high-pressure gases, for example on the order of 1,000 to 10,000 psi. Because the quantities of dosing gas delivered to sample chamber 211-215 are generally small, in some embodiments, the volume of dosing gas reservoir 204 may be relatively low, for example less than about 5 milliliters. Dosing gas reservoir 204 also may include a temperature measuring device 204A, such as a thermocouple. Dosing gas reservoir 204 is recharged and evacuated via inlet/exhaust valve 216, which is configured to fluidly couple gas reservoir 204 to a dosing gas source (not shown) and a vacuum source (not shown) as desired.

Selecting valve 203 is a rotary valve included within the array 210 of sample chambers 211-215, and is adapted to fluidly couple any one of sample chambers 211-215 to manifold 202 by rotating clockwise or counterclockwise until valve opening 203A is aligned with the opening 206 of the desired sample chamber. Because selecting valve 203 is a rotary valve, there is no volume change associated with the opening and closing of selecting valve 203, which improves the accuracy of sorption measurements. Alternatively, selecting valve 203 may be another variety of valve, such as a needle valve, to provide more complete under high pressure, e.g., pressures greater than about 1000 psi. In one embodiment, selecting valve 203 is configured as an array of multiple shut-off valves, such as needle valves or diaphragm valves, rather than a rotary valve. In such a design, one closing valve is dedicated to fluidly coupling and isolating each of sample chambers 211-215 to and from manifold 202. Selecting valve 203 can be operated manually or in an automated fashion by means of an electronic controller, such as a controller 220.

Controller 220 also can be used to control the operation of different aspects of multiple sample tester 200, such as valve operation, pressure and temperature data collection, and/or dosing quantity and frequency. Alternatively, one or more of these aspects of multiple sample tester 200 can be operated manually.

In operation, a different material sample is placed in each of sample chambers 211-215 of multiple sample tester 200. Then, by determining the equilibrium pressure for each sample when exposed to a specific quantity of dosing gas, multiple sample tester 200 effectively performs five gas sorption tests simultaneously. In some embodiments, each of sample chambers 211-215 is evacuated prior to testing to improve accuracy of the gas sorption testing. After evacuation of sample chambers 211-215, dosing gas reservoir 204 is charged with a desired quantity of dosing gas, and isolation valve 205 is opened to manifold 202. Once dosing gas reservoir 204 is fluidly coupled to manifold 202 and pressure transducer 201, the quantity of dosing gas can be determined, since the temperature, volume and pressure of the dosing gas are known. Selecting valve 203 then fluidly couples manifold 202, pressure transducer 201, and dosing gas reservoir 204 to one of sample chambers 211-215 by rotating into alignment with opening 206 of the desired sample chamber. After closing isolation valve 205, selecting valve 203 is rotated to a position that seals the dosed sample chamber, and this process is repeated until all of chambers 211-215 are dosed. In one embodiment, dosing gas reservoir 205 is fully recharged via inlet/exhaust valve 216 prior to the dosing of each of sample chambers 211-215, since the pressure of dosing gas reservoir 205 is drawn down with each dosing. To recharge dosing gas reservoir 205, selecting valve 203 is rotated to a closed position, i.e., a position between the openings 206 of sample chambers 211-215, inlet/exhaust valve 216 opens to fluidly couple dosing gas reservoir 205 to a dosing gas source, and inlet exhaust valve 216 is closes.

After each of sample chambers 211-215 is dosed, isolation valve 205 is closed, and multiple sample tester 200 begins gas sorption measurements by sequentially measuring the pressure in each sample chamber. A pressure measurement of a sample chamber is accomplished by rotating selecting valve 203 into alignment with opening 206 of the desired sample chamber, thereby fluidly coupling pressure transducer 201 to the sample chamber. After a suitable time interval has elapsed for taking an accurate pressure measurement, selecting valve 203 rotates into alignment with opening 206 of the next sample chamber. The process of sample chamber pressure measurement is repeated until each sample chamber has reached equilibrium pressure, i.e., where no more dosing gas is being absorbed/desorbed by the sample positioned therein. Given a series of sample chamber pressure measurements vs. time, such as pressure-time curve 110 illustrated in FIG. 1, one skilled in the art can determine at what point the sample chamber can be considered at equilibrium for the purposes of any particular sorption test.

Once it has been determined that a sample chamber has reached equilibrium pressure, the quantity of dosing gas absorbed/desorbed by the material sample can be calculated as a function of the equilibrium pressure in the sample chamber. This quantity can be determined by one skilled in the art using the ideal gas law or real gas equations, since the temperature and volume of the sample chamber and reservoir chamber is known as well as the starting pressure, i.e., the dosing pressure, and the ending pressure.

In one embodiment, multiple sample tester 200 is configured such that the total internal volume of manifold 202 and selecting valve 203 is insignificantly small relative to the sample chamber volume, i.e., the sample chamber volume is two or more orders of magnitude greater than the internal volume of manifold 202 and selecting valve 203. With such a design, it can be assumed that effectively no cross-pressure is introduced into a sample chamber each time selecting valve 203 and manifold 202 are fluidly coupled to the subsequent sample chamber for a pressure measurement. As persons skilled in the art will recognize, since the internal volume of manifold 202 and selecting valve 203 is insignificant relative to the sample chamber volume, any effect on sample chamber pressure caused by higher or lower pressure present in manifold 202 and selecting valve 203 is too small to have a significant impact on the overall sorption behavior and the determination of concentration of gas sorbed or desorbed by the sample.

In another embodiment, the internal volume of manifold 202 and selecting valve 203 may be more significant relative to the sample chamber volume. With such a design, a compensated dosing gas quantity may be used to prevent inaccurate gas sorption measurements by multiple sample tester 200. Each time selecting valve 203 fluidly couples manifold 202 to a sample chamber, the internal volume of selecting valve 203 and manifold 202 may be brought to the same pressure as the sample chamber to which they are coupled. However, at any given time, the pressure in each sample chamber may be slightly different. Therefore, each time selecting valve 203 fluidly couples manifold 202 to a sample chamber, a volume of gas at the pressure of the previously measured sample chamber may be introduced into the sample chamber, and the total quantity of gas dosed into or removed from the sample chamber pressure may be altered. Because the volume, temperature, and pressure of the gas contained in manifold 202 and selecting valve 203 is known prior to being fluidly coupled to a sample chamber and can be measured in an intermediate position where the manifold 202 is isolated from any other volume, one skilled in the art may readily calculate the quantity of dosing gas introduced or removed from the sample chamber each time a pressure measurement is performed on the chamber. In this way, when the quantity of dosing gas absorbed/desorbed by each material sample is calculated, the result may be corrected in light of the effective dosing that has taken place due to cross-pressure contained in manifold 202 and selecting valve 203.

After it has been determined that all of sample chambers 211-215 have reached equilibrium pressure and the quantity of dosing gas absorbed/desorbed by each sample has been calculated, another round of gas sorption tests can be conducted on the samples contained in sample chambers 211-215. For adsorption/absorption tests, each sample chamber is charged with another dose of dosing gas. For desorption tests, a quantity of dosing gas is removed from each sample chamber. In this fashion, comprehensive data indicating the sorption capacity of the sample material at different equilibrium pressures are collected.

Persons skilled in the art will appreciate that multiple sample tester 200 may also dose each of sample chambers 211-215 at different times, rather than sequentially. For example, once a particular sample chamber reaches equilibrium pressure, the sample chamber can be dosed while the remaining chambers are still approaching equilibrium pressure from the previous dose. Thus, idle time for each of sample chambers 211-215 may be minimized. Similarly, when all dosing of a particular sample is complete, i.e., a PCT curve for the sample has been established, a new sample may be introduced into the now-idle chamber even as dosing to the other chambers is still underway. In one embodiment, a control routine enabled by controller 220 allows such sample change-out and non-sequential dosing procedures to be performed in an automated fashion.

In one embodiment, multiple sample tester 200 may be dose each of sample chamber 211-215 sequentially without a re-charge of dosing gas reservoir 204 after each dosing, thereby decreasing the time required to begin sorption testing of sample chambers 211-215. Such an approach is of particular value when multiple sample tester 200 includes a very large number of sample chambers. Because the pressure in dosing gas reservoir 204 is drawn down after each dosing, a slightly different quantity of the dosing gas will be introduced into each of sample chambers 211-215. However, because the temperature, volume and pressure of the dosing gas are known in each case, persons of skill in the art can readily perform the calculations necessary to compensate for such variations in dosing to each of sample chambers 211-215. Alternatively, controller 220 may be configured to perform the necessary calculations related to different dosing quantities to further automate the process of sorption testing.

In some cases, the sorption rate of a sample is very high and a significant quantity of dosing gas is absorbed by the sample before dosing gas reservoir 204 is fluidly decoupled from the sample chamber in question. Persons skilled in the art will appreciate that multiple sample tester 200 may perform a modified pressure measurement procedure in such cases, to more accurately quantify how much dosing gas is absorbed/desorbed during this time. Namely, multiple pressure measurements may be taken by pressure transducer 201 while dosing gas reservoir 204 is still fluidly coupled to a particular sample chamber after dosing of the sample chamber. In this way, the effect of having the added volume of dosing gas reservoir 204 fluidly coupled to a sample can be compensated for. In one embodiment, controller 220 may be configured to perform such a procedure.

In one embodiment, the internal volume of dosing gas reservoir 204 and each of sample chambers 211-215 is large with respect to the samples undergoing sorption testing. With such a design, multiple sample tester 200 is configured to perform life cycle measurements, in which an individual dose sufficient to fully charge or discharge gas to or from the sample is dosed at one time. With life cycle testing, a sample undergoes a single absorption dose followed by a single desorption dose, and this process is then repeated for a large number of cycles.

Figure 3:
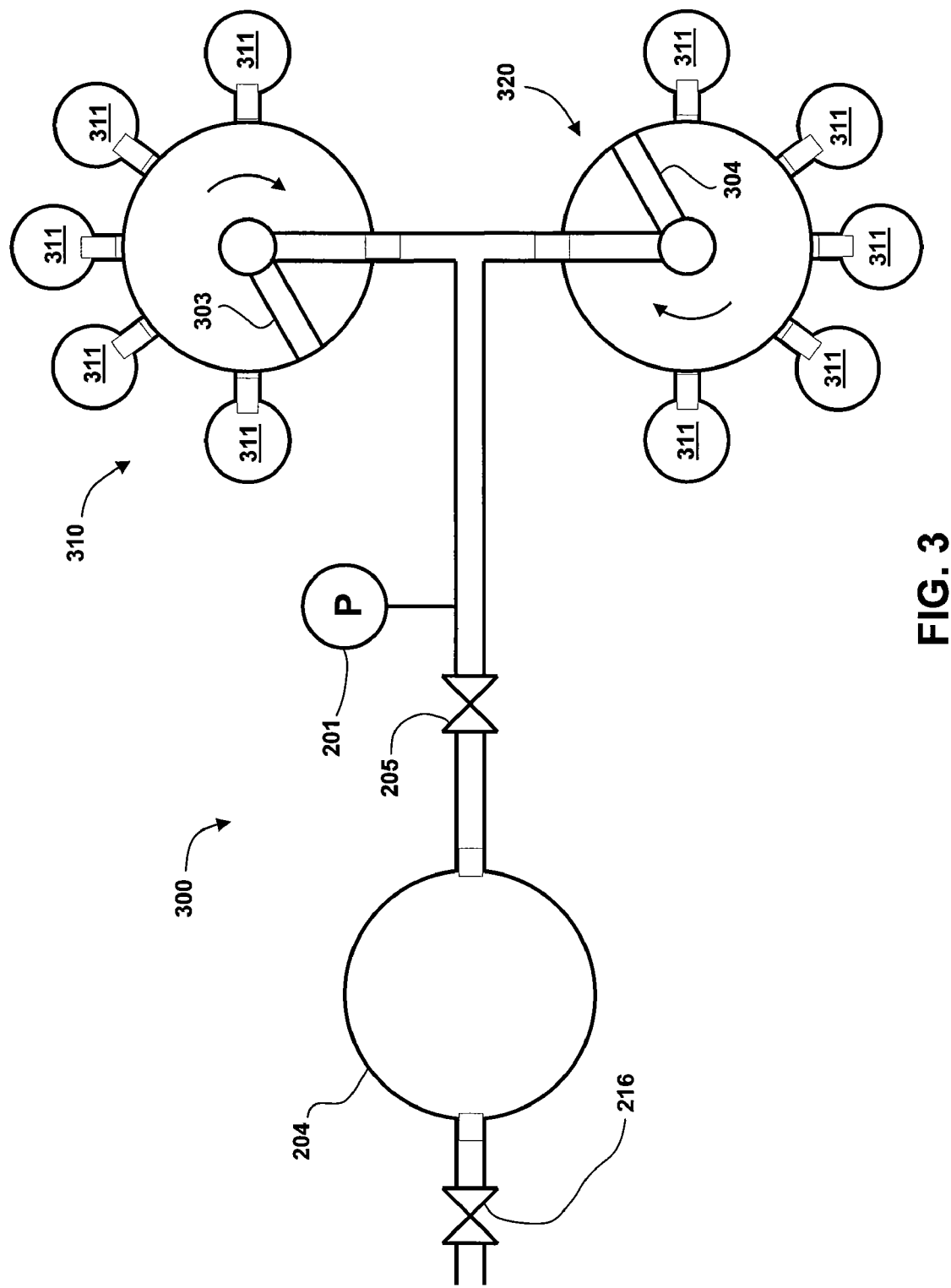
FIG. 3 illustrates a multiple sample tester having two radial arrays and two selecting valves, according to an embodiment of the invention.

Multiple sample tester 200 in FIG. 2 is configured with five sample chambers 211-215, but one skilled in the art will appreciate that a multiple sample tester as described herein can be configured with a large number of sample chambers. FIG. 3 illustrates a multiple sample tester 300 having two radial arrays 310, 320 and two selecting valves 303, 304, according to an embodiment of the invention. In this configuration, only one pressure transducer 201 is required for sorption testing, but a larger number of sample chambers 311 are available for testing.

Figure 4B:
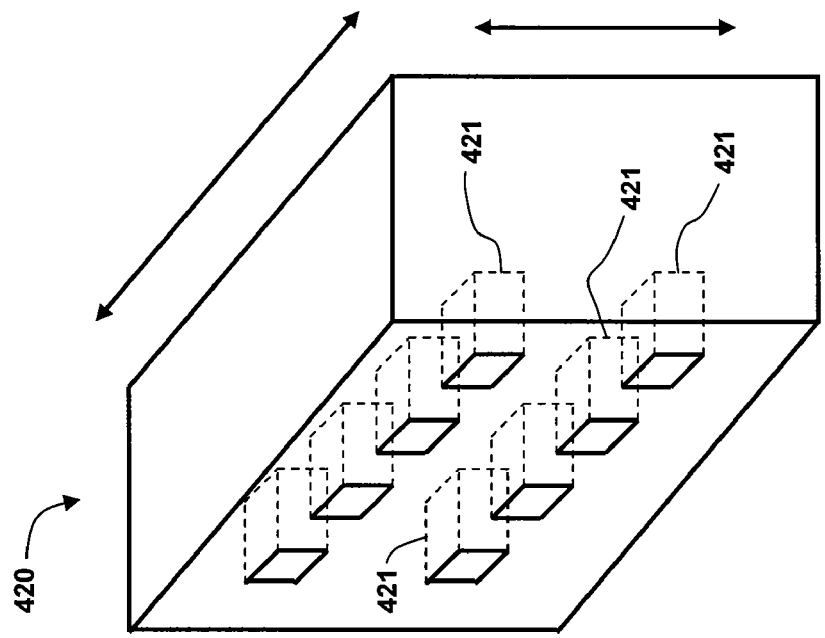
FIG. 4B illustrates a linear array of sample chambers, having multiple rows of sample chambers, according to an embodiment of the invention.
Figure 4A:
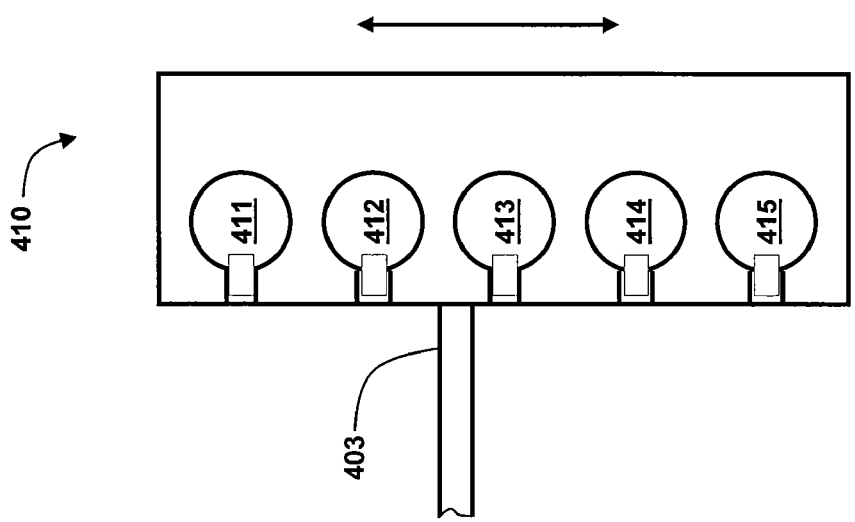
FIG. 4A illustrates a linear array of sample chambers, according to an embodiment of the invention.

In another embodiment, a multiple sample tester includes a linear array of sample chambers. FIG. 4A illustrates a linear array 410 of sample chambers 411-415, according to an embodiment of the invention. Multiple sample tester 200 may be configured with linear array 410 instead of array 210 of FIG. 2. As shown, a slider valve 403 is used to fluidly couple manifold 202 to each of sample chambers 411-415 and linear array 410 is translated horizontally to actuate slider valve 403. Similar a rotating valve, such as selecting valve 203 of FIG. 2, there is essentially no volume displacement associated with slider valve 403 fluidly coupling manifold 202 to any of sample chambers 411-415. FIG. 4B illustrates a linear array 420 of sample chambers 421, having multiple rows of sample chambers, according to an embodiment of the invention. As shown, linear array 420 is translated horizontally and vertically to fluidly couple each of sample chambers 421 to a slider valve.

Figure 5:
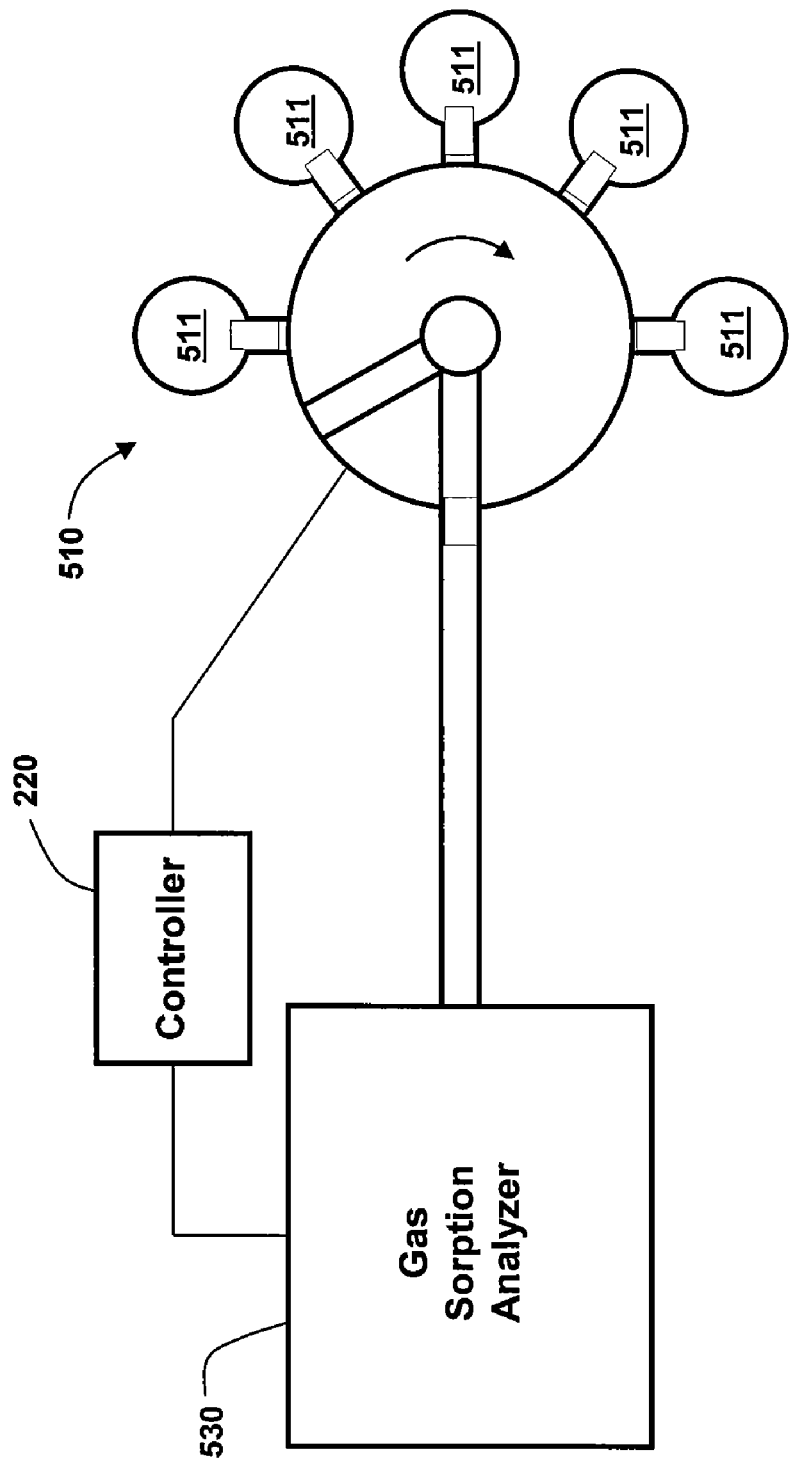
FIG. 5 is a schematic illustration of an array of sample chambers fluidly coupled to a gas sorption analyzer, according to an embodiment of the invention.

In one embodiment, an array of sample chambers is fluidly coupled to a Sieverts' device or other gas sorption analyzer, such as a PCTPro-2000, available from Hy-Energy LLC, Newark, Calif. FIG. 5 is a schematic illustration of an array 510 of sample chambers 511 fluidly coupled to a gas sorption analyzer 530 according to an embodiment of the invention. For automated operation of gas sorption analyzer 530 and array 510, a controller 550 can be used. As shown, array 510 of sample chambers 511 is used to replace the single sample chamber normally used with gas sorption analyzer 530. A dosing gas reservoir and pressure transducer are contained in gas sorption analyzer 530.

Figure 6:
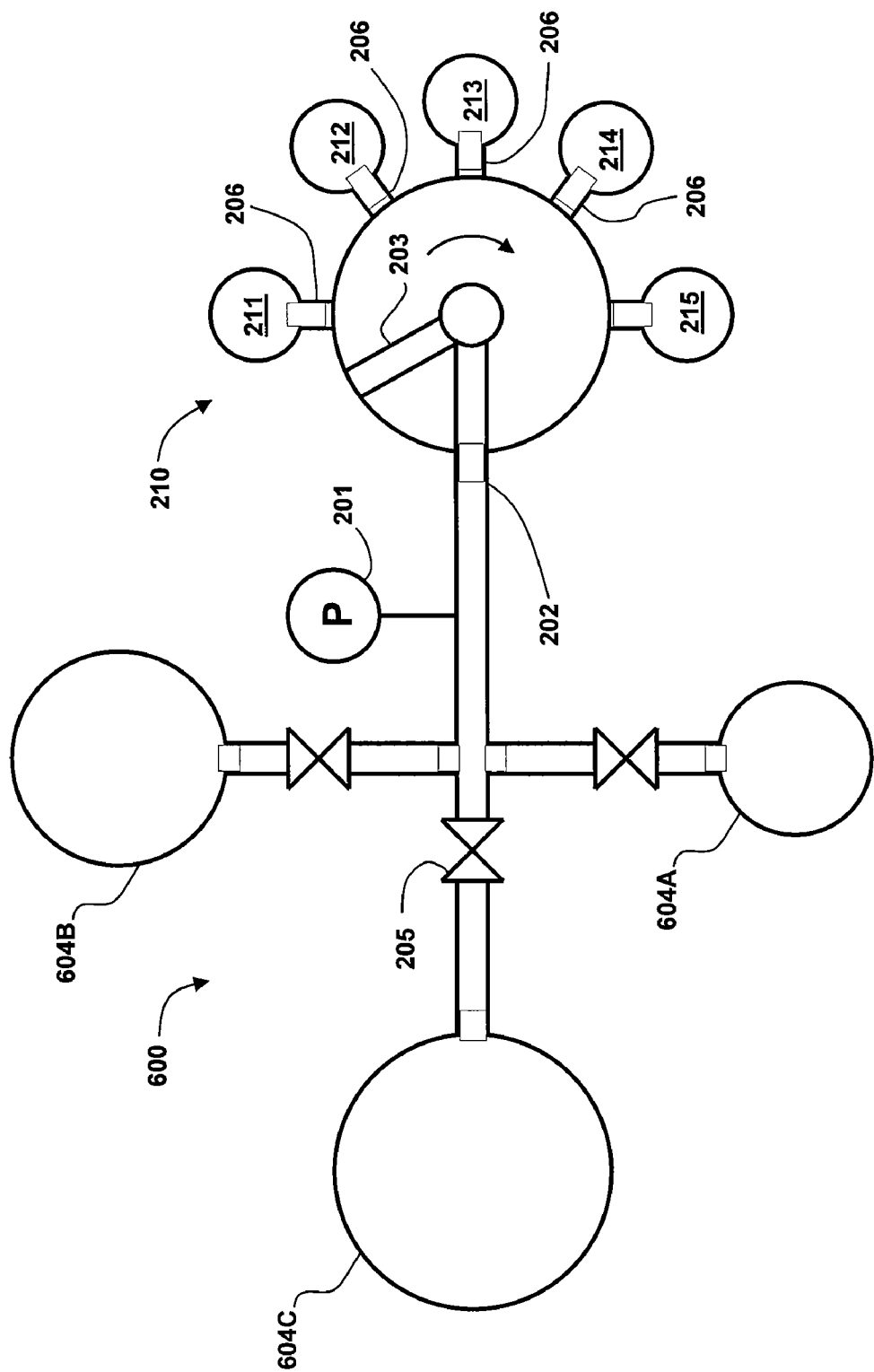
FIG. 6 schematically illustrates a multiple sample tester having three dosing gas reservoirs, according to an embodiment of the invention.

In another embodiment, a multiple sample tester includes multiple dosing gas reservoirs of various volumes to enable full absorption/desorption kinetics measurements. FIG. 6 schematically illustrates a multiple sample tester 600 having three dosing gas reservoirs 604A-C, according to an embodiment of the invention. In this configuration, dosing gas reservoirs 604A has an internal volume on the order of 2× the internal volume of each of sample chambers 211-215, dosing gas reservoirs 604B has an internal volume on the order of 4× the internal volume of each of sample chambers 211-215, and dosing gas reservoirs 604C has an internal volume on the order of 10× the internal volume of each of sample chambers 211-215. With such a design, multiple sample tester 600 can, in addition to the gas sorption tests described above, perform sorption tests that provide full absorption/desorption kinetics data for one or more samples.

While the foregoing is directed to embodiments of the present invention, other and further embodiments of the invention may be devised without departing from the basic scope thereof, and the scope thereof is determined by the claims that follow.

I claim:

1. An apparatus for performing multiple gas sorption measurements comprising:
   an array of sealed sample chambers, wherein at least one of the sealed sample chambers has a calibrated volume and is configured to contain a material sample during a gas sorption test;
   a pressure transducer fluidly coupled to a manifold;
   a selecting valve configured to fluidly couple the at least one of the sample chambers to the manifold, wherein the selecting valve moves to a position that seals the at least one of the sample chambers after gas is introduced into the at least one of the sample chambers; and
   a dosing gas reservoir with an isolation valve configured to fluidly couple and decouple the dosing gas reservoir to and from the manifold.

2. The apparatus of claim 1, wherein the internal volume of a sealed sample chamber is at least 100 times greater than the combined internal volume of the selecting valve and the manifold.

3. The apparatus of claim 2, wherein the manifold comprises a tube having an inner diameter of 2 mm or less.

4. The apparatus of claim 3, wherein the array of sealed sample chambers has a circular configuration.

5. The apparatus of claim 1, wherein the array of sealed sample chambers has a linear configuration.

6. The apparatus of claim 5, wherein the pressure transducer comprises a plurality of pressure transducers having different operating ranges.

7. The apparatus of claim 1, wherein each of the sealed sample chambers is configured with an internal temperature measuring device.

8. The apparatus of claim 1, wherein the selecting valve comprises a rotary valve.

9. The apparatus of claim 1, wherein the selecting valve comprises a sliding valve.

10. The apparatus of claim 1, wherein the selecting valve is further configured to fluidly isolate all of the sealed sample chambers from the manifold.

11. The apparatus of claim 1, wherein the selecting valve is configured was multiple shut-off valves.

12. The apparatus of claim 1, wherein the internal volume of a sealed sample chamber is large enough to contain a quantity of a dosing gas sufficient to fully charge a sample contained in the sealed sample chamber.

13. The apparatus of claim 1, further comprising a second dosing reservoir having an internal volume at least about twice the internal volume of one of the sealed sample chambers.

14. An apparatus for performing multiple gas sorption measurements, comprising:
   an array of sealed sample chambers, wherein at least one of the sealed sample chambers has a calibrated volume and is configured to contain a material sample during a gas sorption test;
   a selecting valve configured to fluidly couple the at least one of the sample chambers to the manifold, wherein the selecting valve moves to a position that seals the at least one of the sample chambers after gas is introduced into the at least one of the sample chambers; and
   a gas sorption analyzer fluidly coupled to the manifold.

15. The apparatus of claim 14, wherein the manifold comprises a tube having an inner diameter of 2 mm or less.

16. The apparatus of claim 15, wherein the array of sealed sample chambers has a circular configuration.

17. The apparatus of claim 14, wherein the array of sealed sample chambers has a linear configuration.

18. The apparatus of claim 14, wherein the selecting valve comprises a rotary valve.

19. The apparatus of claim 14, wherein the selecting valve comprises a sliding valve.

20. The apparatus of claim 14, wherein the selecting valve is further configured to fluidly isolate all of the sample chambers from the manifold.

21. The apparatus of claim 14, further comprising a controller electronically linked to the Sievert's type gas sorption analyzer and the selecting valve and configured to operate the gas sorption analyzer and the selecting valve.

* * * * *